United States Patent
Mezghani et al.

(10) Patent No.: US 12,247,448 B2
(45) Date of Patent: Mar. 11, 2025

(54) SYSTEM AND METHOD FOR AUTOMATED DRILL CUTTING SAMPLING, PREPARATION, ANALYSIS, AND PACKAGING

(71) Applicant: SAUDI ARABIAN OIL COMPANY, Dhahran (SA)

(72) Inventors: Mokhles M. Mezghani, Dhahran (SA); Mustafa Ali H. Al Ibrahim, Safwa (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 233 days.

(21) Appl. No.: 17/456,299

(22) Filed: Nov. 23, 2021

(65) Prior Publication Data

US 2023/0160269 A1     May 25, 2023

(51) Int. Cl.
*E21B 21/06* (2006.01)
*E21B 49/00* (2006.01)
*G01N 33/24* (2006.01)

(52) U.S. Cl.
CPC .......... *E21B 21/066* (2013.01); *E21B 49/003* (2013.01); *G01N 33/24* (2013.01)

(58) Field of Classification Search
CPC ...... E21B 21/066; E21B 49/003; G01N 33/24
See application file for complete search history.

(56) References Cited

U.S. PATENT DOCUMENTS

| 3,563,255 A | 2/1971 | Morris |
| 3,688,781 A * | 9/1972 | Talley, Jr. ............. E21B 21/001 |
| | | 210/216 |

(Continued)

FOREIGN PATENT DOCUMENTS

| CA | 2638405 A1 | 12/2009 |
| CN | 108590535 A | 9/2018 |

(Continued)

OTHER PUBLICATIONS

A. M. Almassri et al. "Pressure Sensor: State of the Art, Design, and Application for Robotic Hand" Journal of Sensors, v. 2015, doi:10. 1155/2015/846487 (13 pages).

(Continued)

*Primary Examiner* — Mohamed Charioui
*Assistant Examiner* — Xiuqin Sun
(74) *Attorney, Agent, or Firm* — Osha Bergman Watanabe & Burton LLP (57) ABSTRACT

A modular system for analyzing drilled cuttings includes a sampler unit, a washer unit, an analysis unit, and a central processing unit. The sampler unit receives the drilled cuttings from a shale shaker disposed on a rig site that obtains the drilled cuttings. The washer unit removes debris from the drilled cuttings. The analysis unit determines lithological properties of the drilled cuttings. The packager unit packages the drilled cuttings. The central processing unit coordinates operations to process the drilled cuttings through each of the sampler unit, washer unit, analysis unit and packager unit. The central processing unit facilitates a processing link among the sampler unit, washer unit, analysis unit and packager unit so that the sampler unit, washer unit, analysis unit and packager unit are integrated to form the modular system.

17 Claims, 6 Drawing Sheets

(56) References Cited

U.S. PATENT DOCUMENTS

| | | | | |
|---|---|---|---|---|
| 4,444,280 | A | * | 4/1984 | Howeth .................. E21B 21/07 |
| | | | | 175/209 |
| 4,546,783 | A | | 10/1985 | Lott |
| 4,836,302 | A | * | 6/1989 | Heilhecker .............. B09B 3/45 |
| | | | | 134/40 |
| 5,454,957 | A | | 10/1995 | Roff, Jr. |
| 5,866,814 | A | * | 2/1999 | Jones .................... E21B 49/00 |
| | | | | 73/152.11 |
| 6,386,026 | B1 | | 5/2002 | Zamfes |
| 6,845,657 | B2 | | 1/2005 | Williams |
| 8,538,697 | B2 | | 9/2013 | Russell et al. |
| 8,967,249 | B2 | | 3/2015 | Akkurt et al. |
| 9,920,623 | B1 | | 3/2018 | Leeper et al. |
| 10,767,477 | B1 | | 9/2020 | Leeper et al. |
| 10,927,671 | B1 | | 2/2021 | Tonner et al. |
| 2020/0018161 | A1 | | 1/2020 | Stepanov et al. |
| 2021/0379511 | A1 | * | 12/2021 | Scott .................... B01D 33/806 |

FOREIGN PATENT DOCUMENTS

| | | | | |
|---|---|---|---|---|
| CN | 112113958 | A | * | 12/2020 |
| EP | 3156587 | A1 | * | 4/2017 |
| JP | 2007220128 | A | * | 8/2007 |
| WO | WO-2005124096 | A1 | * | 12/2005 ............. B65G 53/10 |

OTHER PUBLICATIONS

C. Carpenter "Deep-Learning Techniques Classify Cuttings Volume of Shale Shakers" Journal of Petroleum Technology, v. 72, No. 05, p. 61-62, May 2020, doi:10.2118/0520-0061-JPT (2 pages).

S. K. Clark et al. "Logging Rotary Wells from Drill Cuttings" AAPG Bulletin, v. 12, No. 1, p. 59-76, 1928, doi:10.1306/3D9327DA-16B1-11D7-8645000102C1865D (18 pages).

X. Du et al. "Classifying Cutting Volume at Shale Shakers in Real-Time via Video Streaming Using Deep-Learning Techniques" SPE Drilling & Completion, v. 35, No. 03, p. 317-328, Sep. 2020; doi:10.2118/194084-PA (12 pages).

G. Dunn "Wellsite Math" in Development Geology Reference Manual: American Association of Petroleum Geologists, Methods in Exploration 10, 1992 (5 pages).

D. T. Georgi et al. "Advances in Cuttings Collection and Analysis" SPWLA, 34th Annual Logging Symposium; Jun. 13-16, 1993 (20 pages).

Y. Gidh et al. "WITSML v2.0: Paving the Way for Big Data Analytics Through Improved Data Assurance and Data Organization" in SPE Intelligent Energy International Conference and Exhibition, Aberdeen, Scotland, UK: SPE; Sep. 2016; doi:10.2118/181096-MS (12 pages).

R. Han et al. "Real-Time 3D Computer Vision Shape Analysis of Cuttings and Cavings" in SPE Annual Technical Conference and Exhibition, Dallas, Texas: SPE; Sep. 2018; doi:10.2118/191634-MS (16 pages).

R. E. Jantzen et al. "Wellsite Information Transfer Specification (WITS) for Digital Rig-Site Data" SPE Drilling Engineering, v. 4, No. 04, p. 291-299, Dec. 1989; doi:10.2118/16141-PA (9 pages).

Y. Kubo et al. "Experiments on method for washing drill cuttings: evaluation of soaking, stirring, and milling effects" JAMSTEC Report of Research and Development, v. 22, p. 39-48; Mar. 2016 (10 pages).

W. McKenzie et al. "A New Communications Protocol for Real-Time Decision Making" in SPE Intelligent Energy International Conference and Exhibition, Aberdeen, Scotland, UK: SPE, Sep. 2016; doi:10.2118/181088-MS (9 pages).

A. Nikitin et al. "Automated Mud Logging System as a Cost-Efficient Way of Acquiring Subsurface Data: Results of the Field Trial" SPE; Oct. 2017; doi:10.2118/187387-MS (11 pages).

K. K. Sappati et al. "Piezoelectric polymer and paper substrates: a review" Sensors, v. 18, No. 11, p. 3605; Oct. 24, 2018 (30 pages).

D. Tonner et al. "Automation Provides Unique Insights of the Rock Record and Subsurface Through the Delivery of a Robotic Sample Collection and Analysis Device" in IADC/SPE Drilling Conference and Exhibition, Fort Worth, Texas, USA: SPE; Mar. 2018; doi:10.2118/189680-MS (12 pages).

R. M. Whiteside "Geologic Interpretations from Rotary Well Cuttings" AAPG Bulletin, v. 16, No. 7, p. 653-674, Jul. 1932; doi:10.1306/3D932AA4-16B1-11D7-8645000102C1865D (22 pages).

R. D. Williams et al. "Improved Methods for Sampling Gas and Drill Cuttings" SPE Formation Evaluation, v. 4, No. 02, p. 167-172, Jun. 1989; doi:10.2118/16759-PA (6 pages).

* cited by examiner

SYSTEM AND METHOD FOR AUTOMATED DRILL CUTTING SAMPLING, PREPARATION, ANALYSIS, AND PACKAGING

BACKGROUND

During the process of drilling an oil or gas well, drilled cuttings from the surrounding formation provide near real-time physical data of the subsurface of the well. As such, analysis of the drilled cuttings provides multiple insights into the health of the well and helps determine physical aspects of the well such as potential casing points, perforation zones, and formation tops. This analysis, known in the art as mud logging, is performed by an experienced mud logger by manually cleaning, processing, and packaging the drilled cuttings at specified intervals.

However, mud logging is not without its challenges. Manually gathering and entering data from the analysis of drilled cuttings may introduce errors into the data. Furthermore, gathering data from drilled cuttings requires manually transferring the samples from a drilling rig to a lab station, which may compromise the integrity of the sample data if the drilled cuttings are damaged during the transfer process. Finally, the manual steps of analyzing and transferring drilled cuttings reduces efficiency in the analysis process, which, in turn, hinders the workflow of the drilling operation.

SUMMARY

A modular system for analyzing drilled cuttings includes a sampler unit, a washer unit, an analysis unit, and a central processing unit. The sampler unit receives the drilled cuttings from a shale shaker disposed on a rig site that obtains the drilled cuttings. The washer unit removes debris from the drilled cuttings. The analysis unit determines lithological properties of the drilled cuttings. The packager unit packages the drilled cuttings. The central processing unit coordinates operations to process the drilled cuttings through each of the sampler unit, washer unit, analysis unit, and packager unit. Finally, the CPU facilitates a processing link among the sampler unit, washer unit, analysis unit, and packager unit so that the units are integrated to form the modular system.

A method from analyzing drilled cuttings includes receiving drilled cuttings from a shale shaker disposed on a rig site that obtains the drilled cuttings. The method further includes removing debris from the drilled cuttings, determining lithological properties of the drilled cuttings, packaging the drilled cuttings, and transmitting the lithological properties of the drilled cuttings to a database. The method further includes coordinating operations for processing the drilled cuttings in order to perform the above steps of receiving the drilled cuttings, removing debris, determining lithological properties, packaging the drilled cuttings, and transmitting the lithological properties. Finally, the method includes facilitating a processing link to perform the coordinated operations such that the coordinated operations are performed by a modular system.

BRIEF DESCRIPTION OF DRAWINGS

Specific embodiments of the disclosed technology will now be described in detail with reference to the accompanying figures. Like elements in the various figures are denoted by like reference numerals for consistency. The sizes and relative positions of elements in the drawings are not necessarily drawn to scale. For example, the shapes of various elements and angles are not necessarily drawn to scale, and some of these elements may be arbitrarily enlarged and positioned to improve drawing legibility.

DETAILED DESCRIPTION

Specific embodiments of the disclosure will now be described in detail with reference to the accompanying figures. In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not intended to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In addition, throughout the application, the terms "upper" and "lower" may be used to describe the position of an element. In this respect, the term "upper" denotes an element disposed further from the surface of the Earth than a corresponding "lower" element, while the term "lower" conversely describes an element disposed closer to the surface of the Earth than a corresponding "upper" element. Likewise, the term "axial" refers to an orientation substantially parallel to the well, while the term "radial" refers to an orientation orthogonal to the well. Finally, the terms "vertical" and "lateral" refer to orientations perpendicular and parallel to the surface of the earth, respectively.

In general, one or more embodiments of the disclosure include a system and method for the automated sampling, preparation, analysis, and packaging of drilled cuttings. Specifically, one or more embodiments of this disclosure presents a modular integrated system for sampling, preparing, analyzing, and packaging drill cutting samples. Focus is given to the integration between the subsystems and components to emphasize high-throughput, portability of the equipment, and usability in drilling rigs with a small physical footprint.

As is commonly known in the art, a drilling operation at a well site includes drilling a borehole into a subterranean formation. For the purpose of drilling a new section of the well, equipment on a drilling rig at the well site may suspend and rotate a drill string and drill bit within the wellbore. The drill string is rotated in the surrounding formation relative to the borehole, thus lengthening the well bore and breaking the surrounding formation into smaller pieces, called drilled cuttings.

While cutting the subterranean formation with the drill bit, drilling mud is pumped through the drill string. The drilling mud flows down the drill string and exits into the bottom of the wellbore through nozzles in the drill bit. Drilling mud in the wellbore then flows back to the surface with entrained cuttings in the space between the drill string and the wellbore, where the cuttings are removed from the drilling mud with a shale shaker. Specifically, the shale shaker separates the drilled cuttings from the drilling fluid by running the fluid and entrained drilled cuttings through a vibrating screen, allowing the drilling fluid to be pumped back into the well and reused. The drilled cuttings are retained in the shale shaker, where they may be output to and analyzed by a modular system according to embodiments disclosed herein.

Figure 1:
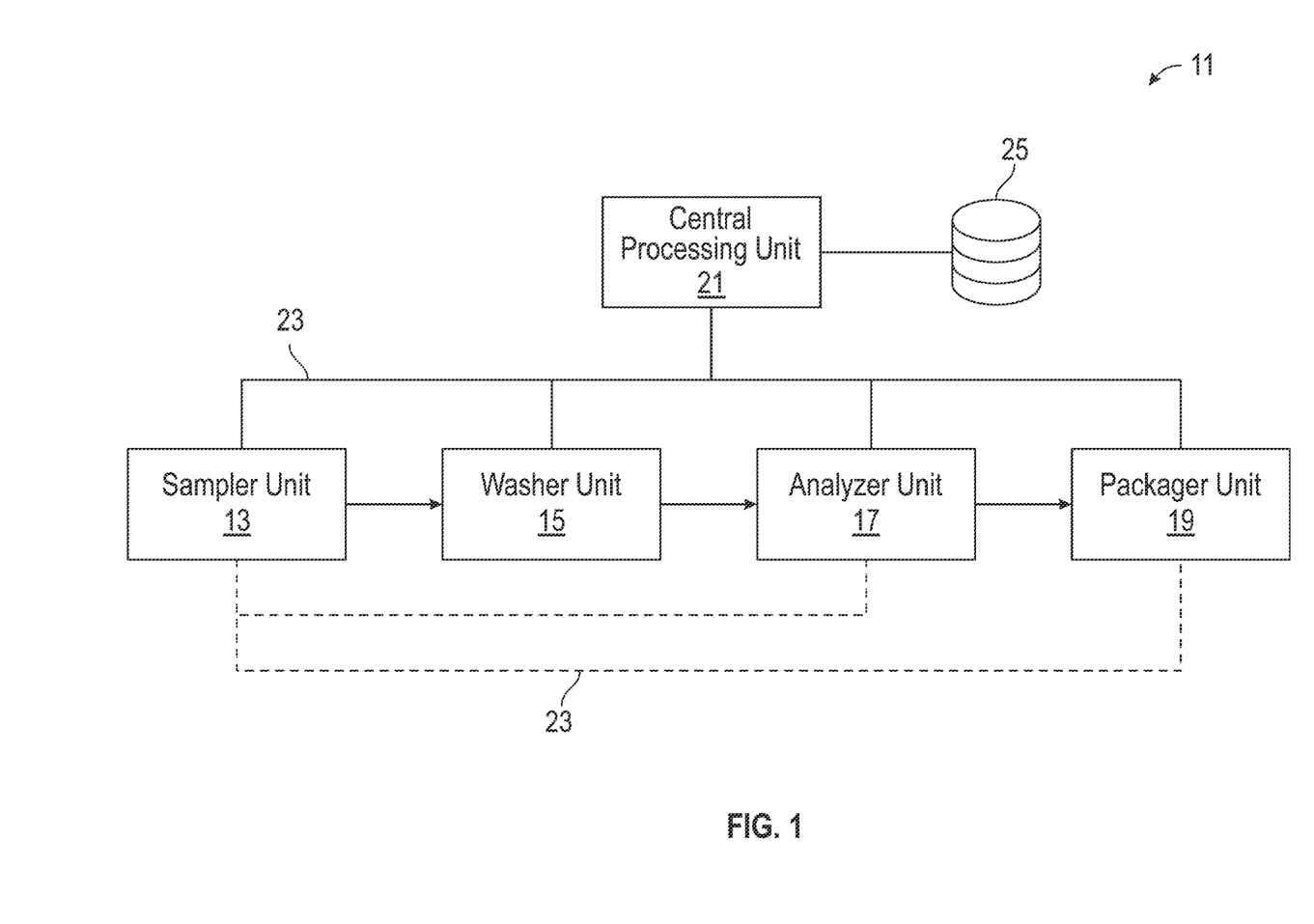
FIG. 1 shows a system overview in accordance with one or more embodiments of the present disclosure.

As shown in FIG. 1, a modular system 11 is primarily composed of four interconnected units that may be operated independently or as a whole, and are transiently installed at a well site for processing drilled cuttings. These units include a sampler unit 13, a washer unit 15, an analyzer unit 17, and a packager unit 19. The units are arranged in sequential manner and are interconnected with a central processing unit 21. The central processing unit 21 includes a processor or plurality of processors, a storage medium and/or a memory, and controls the operation of the sampler unit 13, washer unit 15, analyzer unit 17, and packager unit 19 via a processing link 23. The processing link 23 may be embodied as a wireless connection, such as Bluetooth or Wi-Fi, or may be a physical/wired data connection, such as ethernet, between units. Regardless of the connection between units, the central processing unit 21 coordinates the overall operation of the modular system 11 such that the drilled cuttings 27 are processed through each unit.

During a first step of processing the drilled cuttings, the sampler unit 13 receives and weighs a predetermined amount of drilled cuttings from a shale shaker (e.g., shown in FIG. 2 below). The weighed cuttings are transferred to the washer unit 15, which proceeds to wash the weighed cuttings. From the washer unit 15, the washed cuttings are transferred to the analyzer unit 17, where the washed cuttings are analyzed with a series of sensors that determine the geological properties of the sample. Finally, the analyzed samples are transferred to a packager unit 19 that packages and labels the samples. Concurrently, data generated by the analyzer unit 17 is stored in a database 25, where the data may be reviewed and utilized at a later date.

Figure 2:
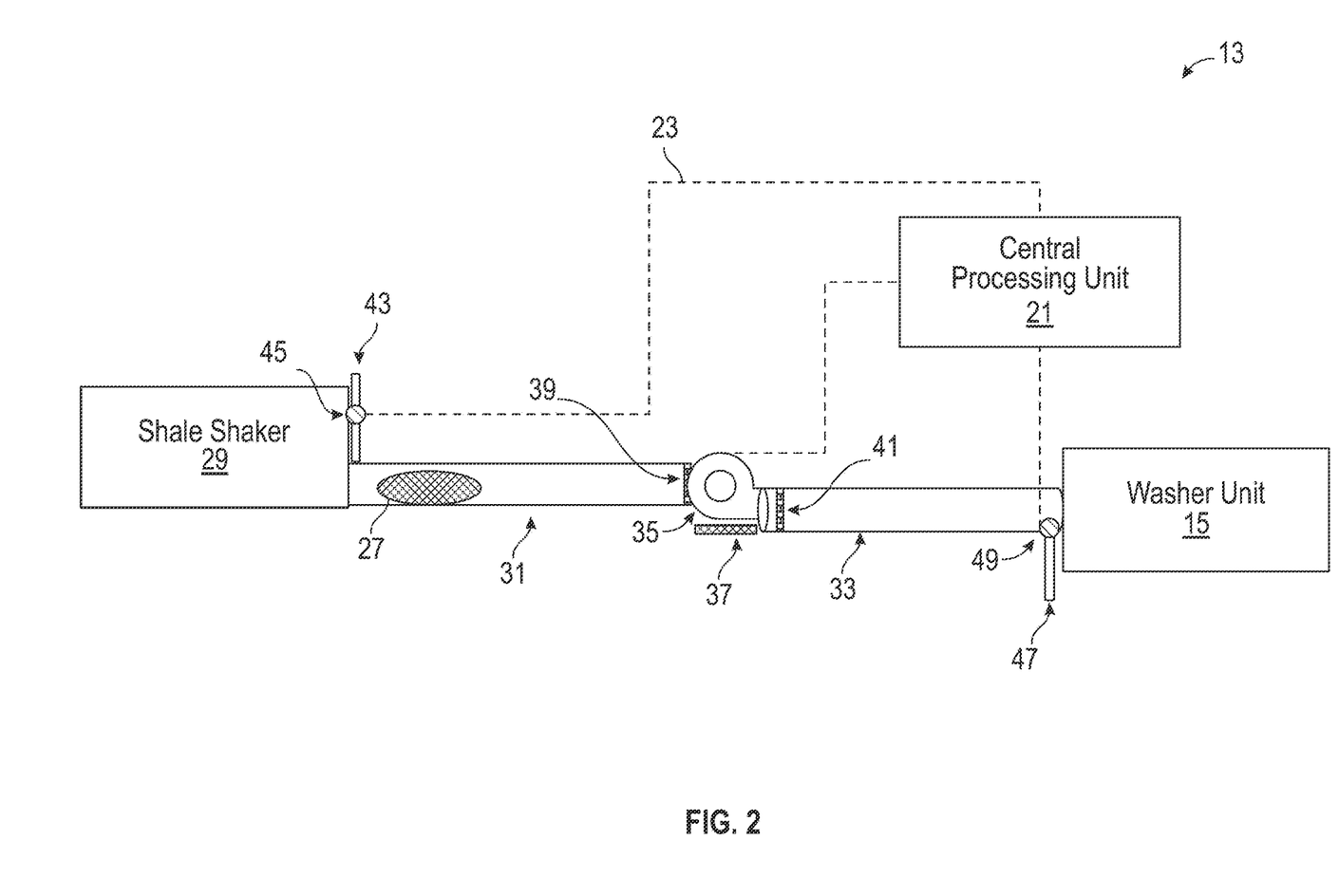
FIGS. 2-5 show various apparatuses in accordance with one or more embodiments of the present disclosure.

FIG. 2 depicts one embodiment of the sampler unit 13. As shown in FIG. 2, the sampler unit 13 is primarily composed of a high viscosity pump 35 and a scale 37, which receive drilled cuttings 27 through a first flexible pipe 31 from a shale shaker 29. In order to adapt to the specific layout of a wellsite, the first flexible pipe 31 is formed from flexible material such as Teflon or other polymers, and is attached to the shale shaker 29 and the high viscosity pump 35 with pipe clamps (not shown). Similarly, a second flexible pipe 33, formed from the same material as the first flexible pipe 31, connects the high viscosity pump 35 to the washer unit 15. Thus, the sampler unit 13 is flexibly connected to the shale shaker 29 at its first end and to the washer unit 15 at its second end, regardless of the location of the shale shaker 29 on a drilling rig.

Continuing with FIG. 2, the high viscosity pump 35 is bordered by an inflow door 39 and an outflow door 41, which serve to facilitate and control the flow of the drilled cuttings 27 through the sampler unit 13. The inflow door 39 and outflow door 41 are rigidly fixed to the high viscosity pump 35 via a motorized hinge connection (not shown). During operation, the motorized hinge connection (not shown) is actuated by the central processing unit 21 such that the inflow door 39 and outflow door 41 rotate upwards on the hinge connection into the first flexible pipe 31 and high viscosity pump 35. By actuating the inflow door 39 and outflow valve 49, the high viscosity pump 35 is fluidly connected to the first flexible pipe 31 and second flexible pipe 33.

Finally, the high viscosity pump 35 rests on top of a scale 37 that weighs the high viscosity pump 35 and the contents thereof. The scale 37 is sandwiched between the high viscosity pump 35 and the ground underneath so that as the high viscosity pump 35 is filled with drilled cuttings 27 the scale 37 can also weigh the drilled cuttings 27. In order to accurately weigh the drilled cuttings 27, the scale 37 is tared to the weight of the high viscosity pump 35 such that the scale 37 naturally discards the weight of the high viscosity pump 35. Consequently, the scale 37 only measures the weight of the drilled cuttings 27 transferred through the sampler unit 13 and disregards the weight of the high viscosity pump 35.

During collection, drilled cuttings 27 are transferred by the shale shaker 29 into the first flexible pipe 31 until the drilled cuttings 27 abut against the inflow door 39. Once the first flexible pipe 31 is filled with the drilled cuttings 27, the inflow door 39 is opened and the high viscosity pump 35 is actuated by the central processing unit 21. Actuation of the high viscosity pump 35 causes the high viscosity pump 35 to fill with the drilled cuttings 27 until the high viscosity pump 35 is completely filled with drilled cuttings 27. At this point, the inflow door 39 is closed and the central processing unit 21 directs the scale 37 to obtain the combined weight of the high viscosity pump 35 and the drilled cuttings 27. After the drilled cuttings 27 are weighed, the outflow door 41 is opened and the drilled cuttings 27 are transferred by the high viscosity pump 35 into the second flexible pipe 33 and the washer unit 15.

In order to clean the first flexible pipe 31, the sampler unit 13 further includes a first cleaning fluid inflow 43 with an inflow valve 45 and a first cleaning fluid outflow 47 with an outflow valve 49. Specifically, the first cleaning fluid inflow 43 is connected to the first flexible pipe 31 at one end at the junction between the shale shaker 29 and the first flexible pipe 31, and is connected to an external fresh water or other cleaning fluid source (not shown, e.g., a holding tank) at its other end. Conversely, the first cleaning fluid outflow 47 is connected at one end to the second flexible pipe 33 at the junction between the washer unit 15 and the second flexible pipe 33, and to a holding tank (not shown) at its other end. After the drilled cuttings 27 are transferred from the high viscosity pump 35 to the washer unit 15, the inflow valve 45 and the outflow valve 49 are actuated and cleaning fluid is introduced from the external source into the first flexible pipe 31, the high viscosity pump 35, and the second flexible pipe 33. The cleaning fluid, as well as any debris entrained within the cleaning fluid from the drilled cuttings 27, then flows out the outflow valve 49 into the holding tank (not shown).

The operation of the central processing unit 21, and thus the sampler unit 13, is controlled and programmed by a mud logger. In particular, a predetermined sampling frequency is determined and adjusted by a mud logger according to the speed of the drilling process and the drilling depth achieved by the drilling rig such that samples are taken at predetermined drilling depths or drilling intervals. The operation of the inflow valve 45 and the outflow valve 49 may also be controlled and predetermined by a mud logger, thereby allowing the complete operation of the sampler unit 13 to be determined prior to initiating a drilling operation. These operations are logged and timestamped by the central processing unit 21, which may be further used by the packager unit 19 in conjunction with the associated weight of the drilled cuttings 27 during the process of labeling the drilled cuttings 27.

Returning to FIG. 2, the central processing unit 21 is configured to control the operation of the inflow door 39 and the outflow door 41 during the transfer of the drilled cuttings 27 according to a predetermined sampling frequency. Furthermore, the central processing unit 21 is configured to open and close the first cleaning fluid inflow 43 and first cleaning fluid outflow 47 according to the operation of the inflow door 39 and the outflow door 41. To achieve this, once the outflow door 41 is opened and the drilled cuttings 27 are transferred to the washer unit 15, the central processing unit 21 actuates the inflow door 39, the outflow door 41, the first cleaning fluid inflow 43, and the first cleaning fluid outflow 47 such that cleaning fluid freely flows through the sampler unit 13.

Figure 3:
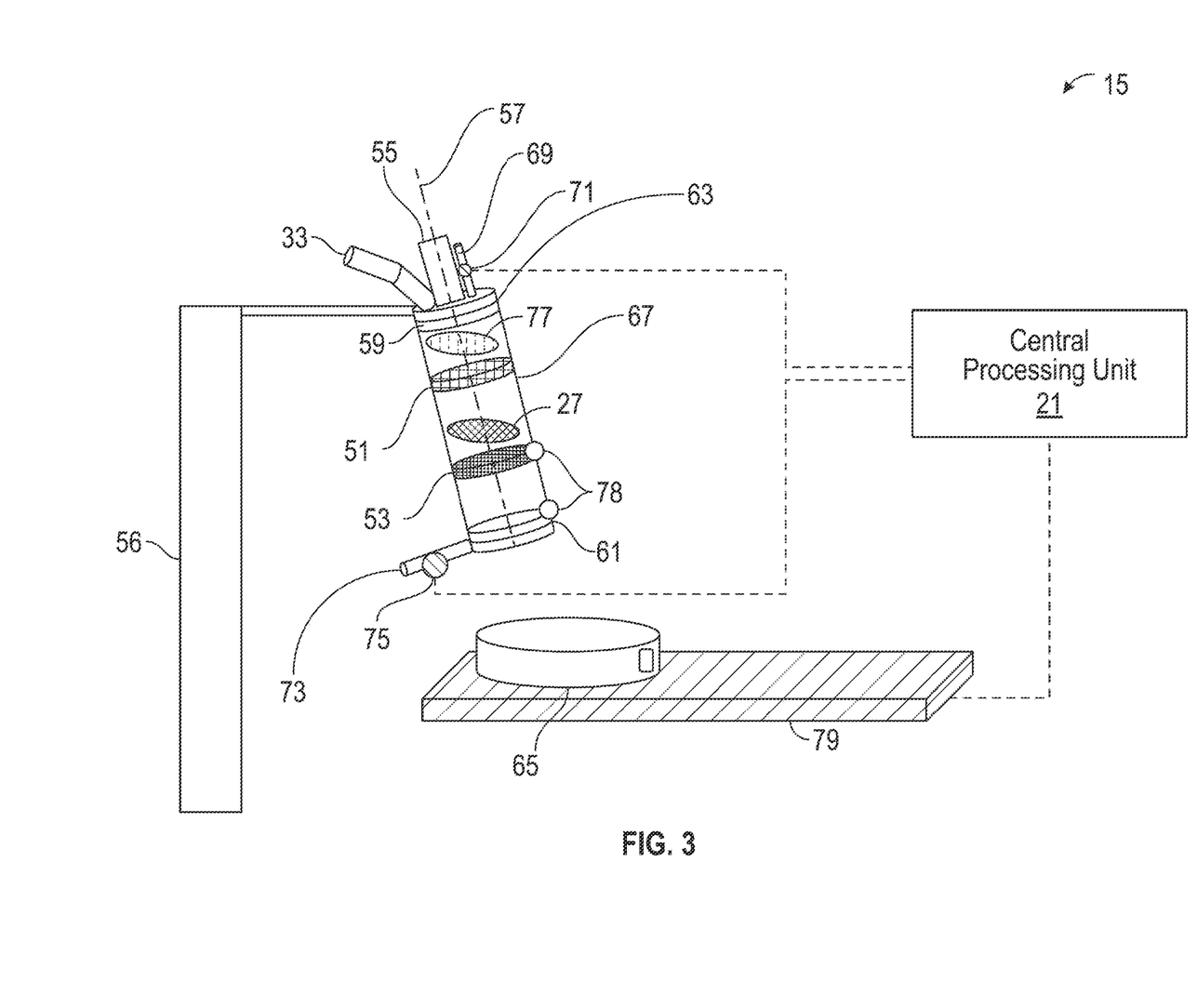

Once the drilled cuttings 27 have been weighed, the drilled cuttings 27 are transferred to a washer unit 15 as depicted in FIG. 3. In particular, FIG. 3 depicts one embodiment of a washer unit 15 that receives drilled cuttings 27 from the sampler unit 13, removes debris 77 from the drilled cuttings 27, and transfers the washed drilled cuttings 27 to the analyzer unit 17.

To achieve this purpose, the washer unit 15 receives drilled cuttings 27 from the second flexible pipe 33 into a casing 67, where the drilled cuttings 27 are filtered through a first sieve 51 until they abut against a second sieve 53. The washer unit 15 is then rotated via a motor 55 around a central axis 57 while fluid is pumped from an external source (not shown) into the washer unit 15, thus removing debris 77 from the drilled cuttings 27. Finally, the washed drilled cuttings 27 are transferred from the washer unit 15 and placed in a sample tray 65 for further analysis at the analyzer unit 17. The orientation and configuration of the various components that make up the washer unit 15 are described below.

To properly filter debris 77 from the drilled cuttings 27, the first sieve 51 and second sieve 53 are disposed within the casing 67 in succession with each other and coaxial with the central axis 57 such that the first sieve 51 is directly above the second sieve 53. The first sieve 51 and the second sieve 53 are each formed from metal wire mesh, where the size of the openings in the mesh are determined according to the anticipated size of the drilled cuttings 27 to be filtered. Specifically, the first sieve 51 is formed of a metal wire mesh with openings that are larger than the average size of the drilled cuttings 27 so that drilled cuttings 27 can easily pass through the first sieve 51 while large debris 77 is trapped between the first sieve 51 and the first endcap 59. Conversely, the size of the openings in the metal wire mesh of the second sieve 53 is smaller than the average size of the drilled cuttings 27 so that the drilled cuttings 27 are trapped by the second sieve 53 and small debris is transferred out of the washer unit 15.

The first endcap 59 and the second endcap 61 are formed of two pieces connected with a rotary union 63. As shown in FIG. 3, the exterior upper half of the first endcap 59 is connected to the second flexible pipe 33, the motor 55, a second cleaning fluid inflow 69, and a stand 56 that fixes the first endcap 59 to the ground such that the washer unit 15 remains stationary and vertically oriented during the rotation of the casing 67. Similarly, the exterior lower half of the second endcap 61 is connected to a second cleaning fluid outflow 73 and remains stationary while the casing 67 rotates. The interior halves of the first endcap 59 and the second endcap 61 are attached to the casing 67 using a variety of methods, as described below. Therefore, due to the rotary union 63 between the exterior and interior halves of the first endcap 59 and the second endcap 61, the casing 67 and drilled cuttings 27 freely rotate around the central axis 57 when the casing 67 is actuated by the motor 55.

In order to create the rotation that filters debris 77 from the drilled cuttings 27 through the first sieve 51 and second sieve 53, the motor 55 is disposed on the upper axial end of the washer unit 15. The motor 55 is attached through the exterior half of the first endcap 59 to the interior half of the first endcap 59 so that as a shaft of the motor 55 rotates, the interior half of the first endcap 59, and thus the casing 67, rotates about the central axis 57. Thus, when the shaft of the motor 55 rotates, the casing 67 and its contents rotate about the central axis 57 of the washer unit 15 due to the connection between the motor 55 and the first endcap 59.

Finally, in order to forcibly filter debris 77 from the drilled cuttings 27, the washer unit 15 includes a second cleaning fluid inflow 69 and a second cleaning fluid outflow 73, which respectively include a second inflow valve 71 and a second outflow valve 75. The second cleaning fluid inflow 69 is attached at one end to the first endcap 59, and at a second end to an external cleaning fluid source (not shown). Similarly, the second cleaning fluid outflow 73 is attached to the second endcap 61 at a first end, and connected to an external tank (not shown) at its other end. Depending on the location of the external tanks, the required length and orientation of the second cleaning fluid inflow 69 and the second cleaning fluid outflow 73 may vary, and, thus, the second cleaning fluid inflow 69 and the second inflow valve 71 are formed of flexible materials such as Teflon, plastic, or equivalent.

Therefore, washing of the drilled cuttings 27 is achieved by the washer unit 15 through the use of the first sieve 51, the second sieve 53, the motor 55, the second cleaning fluid inflow 69, and the second inflow valve 71. Specifically, as discussed above, the drilled cuttings 27 are received from the sampler unit 13 into the casing 67, where large debris 77 (e.g., borehole cave-in debris) are filtered by a first sieve 51. The drilled cuttings 27 move through the openings in the first sieve 51 until they abut against the second sieve 53, at which point the drilled cuttings 27 are washed with fluid from an external water source. To introduce cleaning fluid into the casing 67, the second inflow valve 71 is opened by the central processing unit 21, causing cleaning fluid to move over the drilled cuttings 27 and exit through the second cleaning fluid outflow 73.

Following the removal of the debris 77 from the drilled cuttings 27, the drilled cuttings 27 are removed from the casing 67 by detaching the second endcap 61 and transferring the drilled cuttings 27 from the casing 67 to the sample tray 65. To facilitate this, the second sieve 53 and the second endcap 61 are attached with motorized hinge connections 78 that are controlled by the central processing unit 21. Initially, the second endcap 61 is opened by actuating the motorized hinge connection 78 and dumping the small debris between the second sieve 53 and the second endcap 61 into a sample tray 65, which may be discarded by an operator or mud logger. Next, the motorized hinge connection 78 of the second sieve 53 is actuated, thereby transferring the drilled cuttings 27 to the sample tray 65.

Alternatively, and although not depicted in FIG. 3, a motorized hinge connection 78 may be connected to the first endcap 59 and a second motor (not shown) may be connected to the casing 67, both of which are controlled by the central processing unit 21. In said situations, only a single first sieve and endcap are used to filter the drilled cuttings 27, and the casing 67 is rotated through the central axis 57 by the second motor (not shown) while the first endcap 59 is opened such that the drilled cuttings 27 are dumped into the sample tray 65.

Finally, the motorized hinge connection 78 may not be implemented at all. In such embodiments, the first endcap 59 and second endcap 61 are attached to the casing 67 by pressing, with interference, the first endcap 59 and second endcap 61 into the casing 67. Such can be seen in FIG. 3, where the first endcap 59 is attached to the casing 67 with a press-fit connection. The first endcap 59 and second endcap 61 are manually removed following a washing operation and the drilled cuttings 27 are transferred to the sample tray 65 by an operator.

Regardless of the specific method used to transfer the drilled cuttings 27 to the sample tray 65, the sample tray 65 is then transferred from the washer unit 15 to the analyzer unit 17 with the drilled cuttings 27 via a first conveyor belt 79, where the drilled cuttings 27 are further analyzed.

Figure 4:
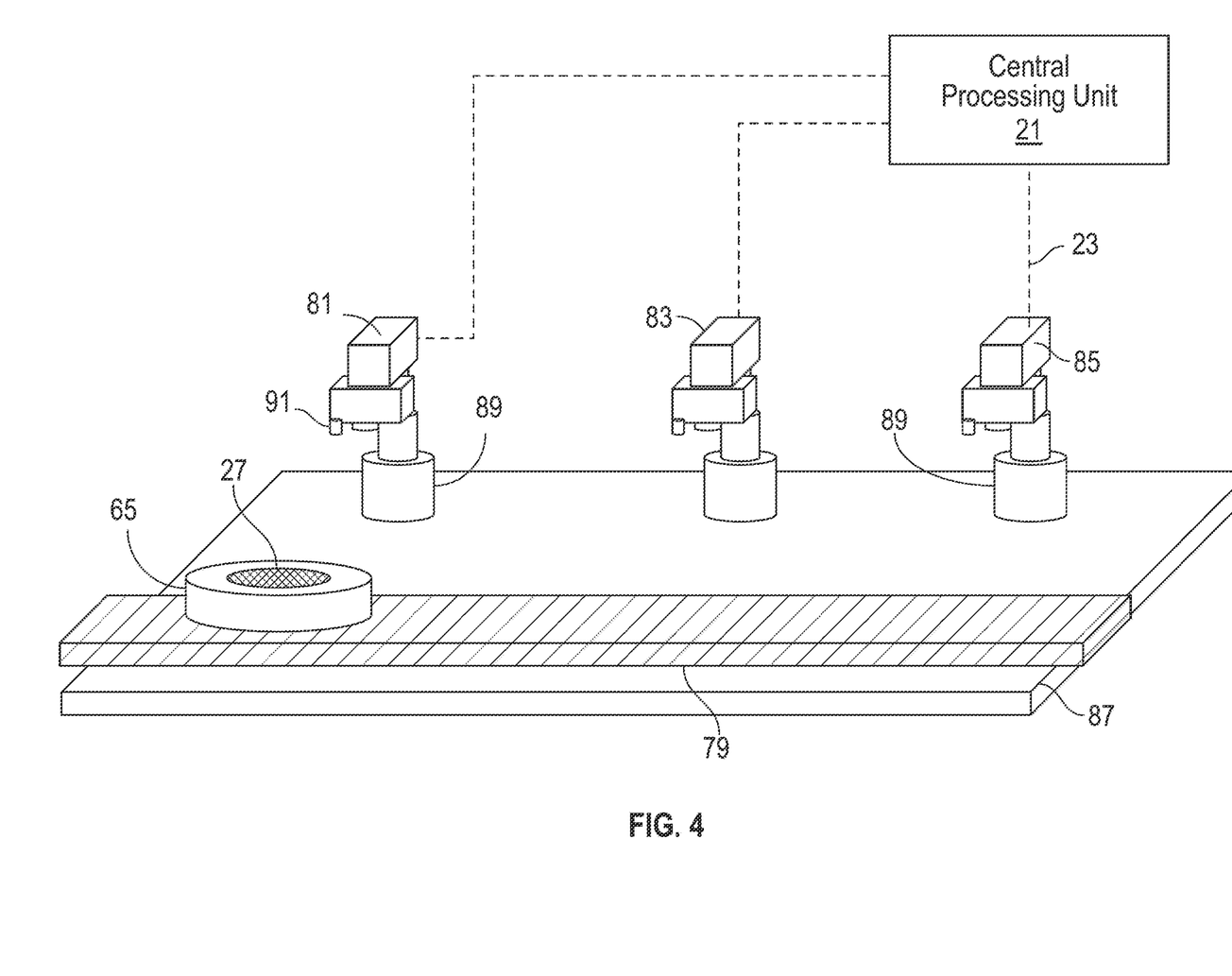

As shown in FIG. 4, the analyzer unit 17 includes a plurality of sensors that are each configured to sample the drilled cuttings 27 in order to determine the lithological properties thereof. By way of non-limiting example and as shown in FIG. 4, the sensors of the analyzer unit 17 include an ultraviolet (UV) camera 81, an infrared camera 83, and an X-Ray Frequency (XRF) spectrometer 85, all of which are commonly known in the art and not described herein for the sake of brevity. Each sensor is disposed on a respective retractable stand 89, which is fixed to a working surface 87 at the height of the first conveyor belt 79.

During analysis, the sample tray 65 and drilled cuttings 27 are transferred between sensors using the first conveyor belt 79 such that each sensor may analyze properties of the drilled cuttings 27. However, due to variations in the required distance between a specific sensor and the drilled cuttings 27, the height of each sensor must be individually adapted to the height of the drilled cuttings 27. To remedy the above situation, the plurality of sensors are each disposed on retractable stands 89 that move vertically in relation to the first conveyor belt 79 to adjust the height of the individual sensor to the height of the drilled cuttings 27. Each retractable stand 89 includes a proximity sensor 91, which calculates, in conjunction with the central processing unit 21, the height of a respective retractable stands 89 from the first conveyor belt 79.

The retractable stand 89 is actuated according to commands from the central processing unit 21, which receives and transfers data from the retractable stands 89 via the processing link 23. Multiple actuation mechanisms may be used to actuate the retractable stands 89. For example, a retractable stand 89 may include a motor, gearbox, and either a rack-and-pinion gear or a worm gear. Alternatively, the retractable stands 89 may be hydraulically actuated using a piston and cylinder arrangement arranged within the retractable stands 89, or electromagnetically actuated with a solenoid. Regardless of the actuation mechanism used, once the retractable stands 89 are adjusted to the required height to measure the drilled cuttings 27, the sensors capture data of the drilled cuttings 27 as described below.

Each sensor is configured to aid in determining properties of the drilled cuttings 27 by cataloging frequencies emitted and reflected by the drilled cuttings 27. The captured frequencies are submitted to the central processing unit 21, which compares the captured frequencies, using a neural network, against sample data stored in the database 25 and determines properties of the drilled cuttings 27 based on the sample data. Specific properties of the drilled cuttings that are captured by the sensors and analyzed by the central processing unit 21 include the grain pattern, shape, porosity, chemical composition, and lithology of the drilled cuttings 27, which are stored in the database 25 (e.g., shown in FIG. 1) for use by the packager unit 19.

Although not depicted in FIG. 4, it is envisioned within the scope of the disclosure that the plurality of sensors include multiple other sensors used to analyze the drilled cuttings 27. To this end, cameras with automated algorithms may be used to monitor the drilled cuttings 27 and ensure that the drilled cuttings 27 are not damaged by other sensors. Moreover, brightfield cameras, hyperspectral cameras, camera flashes, piezoelectric sensors or other touch sensors, hygrometers, and electron microscopes may be used in place or in addition to the aforementioned sensors.

Figure 5:
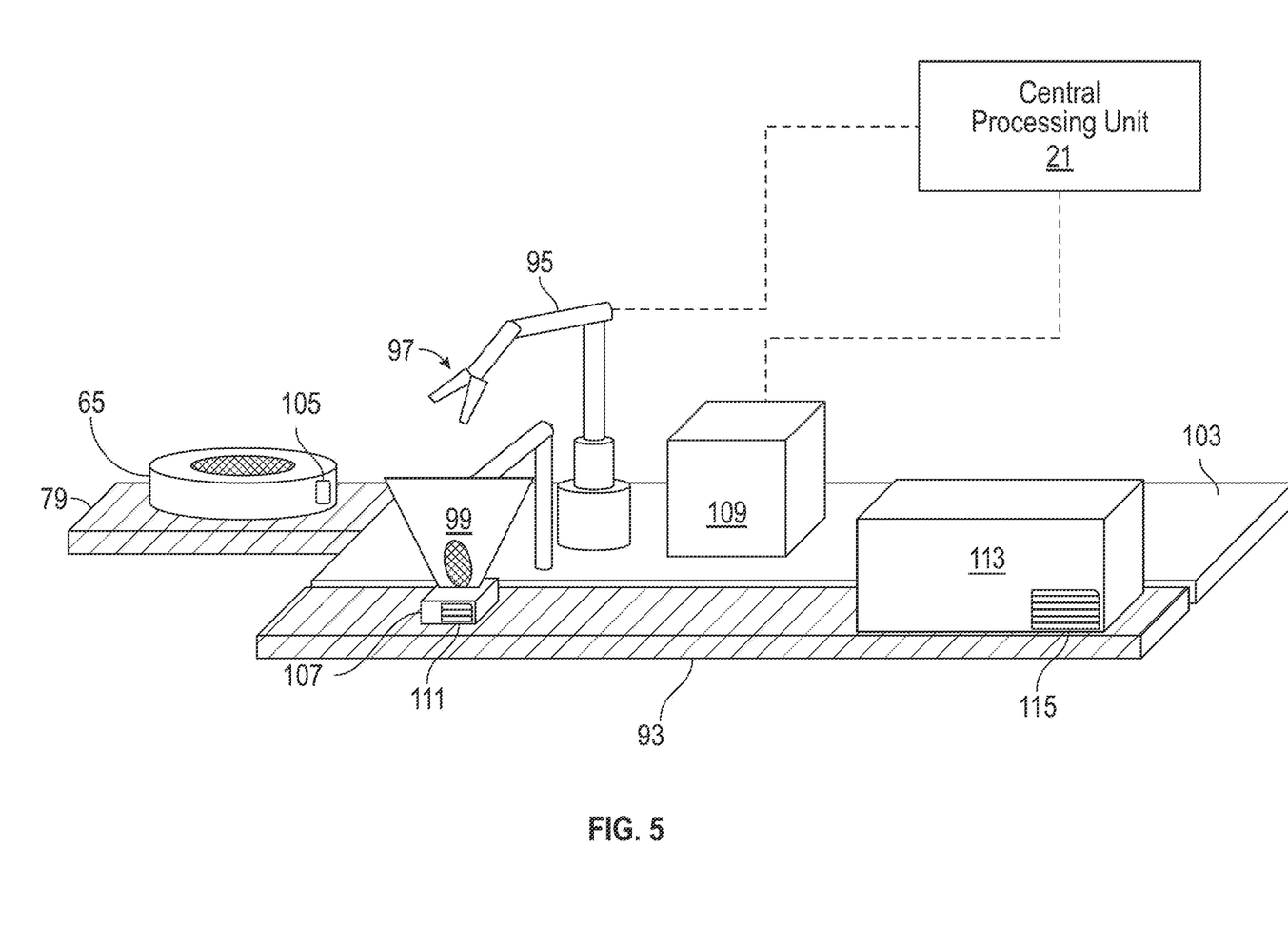

Once the drilled cuttings 27 have been analyzed by each sensor, the drilled cuttings 27 and sample tray 65 are transferred with the conveyor belt to the packager unit 19, as shown in FIG. 5.

FIG. 5 depicts one embodiment of the packager unit 19. As seen in FIG. 5, the packager unit 19 includes a second conveyor belt 93, a robotic arm 95, a funnel 99, and a printer 109. The robotic arm 95, the funnel 99, and the printer 109 are each fixed to a second working surface 103, such as a work table, which is located at the same height as the first conveyor belt 79 and the second conveyor belt 93.

Initially, a sample tray 65 with the drilled cuttings 27 is brought to the robotic arm 95 from the analyzer unit 17, where the robotic arm 95 grips the sample tray 65 with an end effector 97. The end effector 97 is formed from two complimentary jaws that are jointed together and controlled by a motor or servo (not shown) according to instructions from the central processing unit 21. The jaws of the end effector 97 are sized in conjunction with a holding groove 105 on the exterior of the sample tray 65 such that the end effector 97 grips the holding groove 105 throughout the packaging process regardless of the orientation of the sample tray 65. Furthermore, the inner faces of the jaws are lined with rubber or other high-friction material that aids in gripping the sample tray 65.

Once the end effector 97 has been closed around the holding groove 105 by the central processing unit 21, the robotic arm 95 proceeds to lift the sample tray 65, rotate to the funnel 99, and rotate the sample tray 65 so that the drilled cuttings 27 are transferred into a sample package 107 via the funnel 99. The sample package 107 may be formed from cardboard or low density polyethylene (LDPE), while the funnel 99 may be formed from stainless steel, plastic, or other suitable materials. As shown, the funnel 99 is fixed to the second working surface 103 and arranged such that the output of the funnel 99 is directly above the sample package 107 and second conveyor belt 93. After transferring the contents of the sample tray 65 to the sample package 107, the robotic arm 95 places the sample tray 65 in a stack at the edge of the second working surface 103 to ease the removal of sample trays from the analyzer unit 17.

To label the sample package 107, a printer 109 that prints a package label 111 is located next to the robotic arm 95. The package label 111 contains information stored on the database 25 of the central processing unit 21 relevant to the drilled cuttings 27, such as the date and time of origin, sampling depth, weight, and operator notes concerning significant features uncovered during analysis. Furthermore, the package label 111 may include an adhesive backing so that the package label 111 may be easily adhered to the sample package 107. Alternatively, the sample package 107 may include a container (not shown), such as a plastic bag or envelope, that the package label 111 is retained in. Thus, in order to apply the package label 111 to the sample package 107, the robotic arm 95 lifts the package label 111 from the printer 109 and adheres the package label 111 to the sample package 107 according to the specific adhesion method.

Once the sample package 107 is labeled, the sample package 107 is placed by the robotic arm 95 in a sample container 113. The sample container 113 is then also labeled with a container label 115 containing information indicating the rig site at which multiple samples are taken, a range of dates and sampling depths that correspond to the drilled cuttings 27 and the sample package 107, and other information useful for categorizing and distinguishing differing drilled cuttings samples. After the sample container 113 is filled with sample packages 107 and labeled by the robotic arm 95, the sample container 113 is removed from the second conveyor belt 93 by an operator at the rig, and is replaced with a new sample container. Similar to the sample package 107, the sample container 113 may be formed from cardboard, LDPE, or equivalent.

Figure 6:
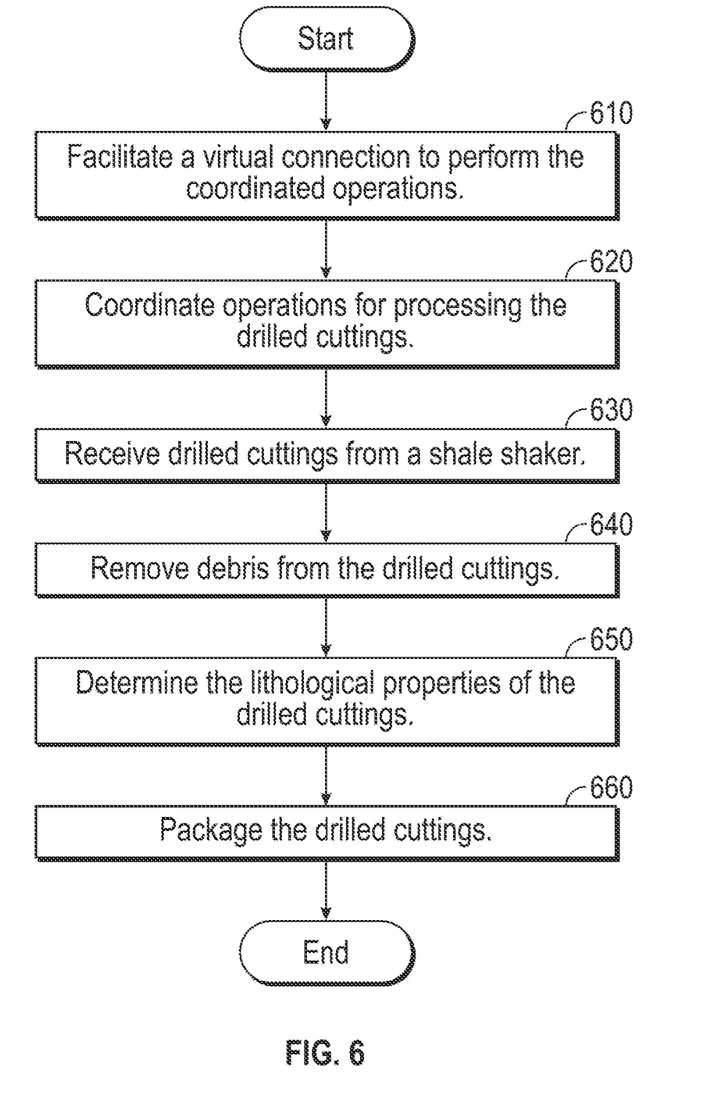
FIG. 6 shows a flowchart of a method in accordance with one or more embodiments of the present disclosure.

FIG. 6 depicts a flowchart showing a method of analyzing drilled cuttings. While the various flowchart blocks in FIG. 6 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

In block 610, a processing link 23 is initialized via the central processing unit 21 in order to interconnect the sampler unit 13, the washer unit 15, the analyzer unit 17, and the packager unit 19 via a virtual connection. The processing link 23 may be embodied as a wireless connection, such as Bluetooth or Wi-Fi, or may be a physical data connection, such as ethernet, between units. Due to the processing link 23, the sampler unit 13, the washer unit 15, the analyzer unit 17, and the packager unit 19 are controlled by the central processing unit 21, and thus form a modular system 11 for analyzing the drilled cuttings and performing coordinated operations.

In block 620, the central processing unit 21 coordinates operations to process the drilled cuttings 27 through the sampler unit 13, washer unit 15, analyzer unit 17 and packager unit 19 as detailed in blocks 630-660. Specifically, the central processing unit 21 controls the intake, sampling, washing, analysis, and packaging of the drilled cuttings 27 by actuating the constituent elements of the individual units. To achieve this, the central processing unit 21 includes a processor or series of processors, a storage medium, and a memory, and controls the operation of the sampler unit 13, washer unit 15, analyzer unit 17, and packager unit 19 via a processing link 23.

In block 630, drilled cuttings 27 are received from a shale shaker 29. In particular, the sampler unit 13 receives and weighs a predetermined amount of drilled cuttings from the shale shaker 29 via a high viscosity pump 35 and a scale 37. In order to weigh the drilled cuttings 27, the high viscosity pump 35 is disposed on top of the scale 37 such that the scale 37 weighs both the drilled cuttings 27 and the high viscosity pump 35 and discards the weight of the high viscosity pump 35. With the aid of the high viscosity pump 35, the sampler unit 13 transfers drilled cuttings 27 from the shale shaker 29 to a washer unit 15 via a first flexible pipe 31 and a second flexible pipe 33.

In block 640, a washer unit 15 removes debris 77 from the drilled cuttings 27. To achieve this, the washer unit 15 receives drilled cuttings 27 from the sampler unit 13 into a casing 67 containing a first sieve 51 and a second sieve 53 that are disposed coaxial with a central axis 57 of the washer unit 15. The washer unit 15 is rotated with a motor 55 around the central axis 57 while fluid is pumped from an external source into the washer unit 15, thus removing debris 77 from the drilled cuttings 27. Subsequently, the washed drilled cuttings 27 are removed from the washer unit 15 by detaching a second endcap 61 from the casing 67 and transferring the drilled cuttings 27 into a sample tray 65.

In block 650, the analyzer unit 17 determines the lithological properties of the drilled cuttings. Specifically, the analyzer unit 17 includes multiple sensors such as a white light camera, an ultraviolet camera, and an x-ray frequency spectrometer that capture the infrared, ultraviolet, and x-ray frequencies of the drilled cuttings. The frequencies emitted and reflected by the drilled cuttings are compared against information stored in the database 25 in order to determine the grain pattern, shape, porosity, chemical composition, and lithology of the drilled cuttings 27.

In block 660, the drilled cuttings 27 are packaged by the packager unit 19. The packager unit 19 includes a second conveyor belt 93, a robotic arm 95, a funnel 99, and a printer 109. A sample tray 65 with the drilled cuttings 27 is brought to the robotic arm 95, where the robotic arm 95 grips the sample tray 65 with an end effector 97. Once the end effector 97 has been closed around the holding groove 105 by the central processing unit 21, the robotic arm 95 proceeds to lift the sample tray 65, rotate, and dump the drilled cuttings 27 into a sample package 107 via the funnel 99. The robotic arm 95 then lifts a package label 111 from the printer 109, adheres the package label 111 to the sample package 107, and places the sample package 107 in a sample container 113, thereby completing the processing of the drilled cuttings.

Accordingly, the aforementioned embodiments as disclosed relate to devices and methods useful for analyzing drilled cuttings.

Specifically, by forming a modular system for analyzing drilled cuttings from multiple units interconnected with flexible joints (e.g., conveyor belts, flexible piping), the system is advantageously capable of receiving drilled cuttings directly from a shale shaker and perform all analysis of the drilled cuttings at the drilling site. Furthermore, by receiving drilled cuttings directly from a shale shaker and analyzing the drilled cuttings at a drill site, the modular system provides instantaneous real-time feedback of the health of the wellbore. Finally, by analyzing drilled cuttings using flexible piping, conveyor belts, sieves, and other elements that accommodate the unique shapes of the drilled cuttings and the drilling rig, the grain type, porosity, and lithology of the drilled cuttings may be analyzed without needing to first grind and transport the samples.

Although only a few embodiments of the invention have been described in detail above, those skilled in the art will readily appreciate that many modifications are possible in the example embodiments without materially departing from this invention. For example, it is easily envisioned that the modular system may be utilized within a laboratory or other environment, and samples are input directly into the washer unit or sampler unit. Alternatively, the system may be broken into individual or combined units, where the sampler and washer unit are disposed at the shale shaker, while the analysis unit and packager unit are located at a separate facility, and the drilled cuttings are manually transferred therebetween. As a third example, cameras with automated algorithms may be used to monitor the workflow and stop the system if a malfunction occurs in any individual unit, or if drilled cuttings are not properly transferred between units. Accordingly, all such modifications are intended to be included within the scope of this disclosure as defined in the following claims.

What is claimed is:

1. A modular system for analyzing drilled cuttings, the modular system comprising:
   a sampler unit comprising:
     a first flexible pipe configured to receive the drilled cuttings from a shale shaker disposed on a rig site and configured to obtain the drilled cuttings;
     a high viscosity pump fluidly connected to the first flexible pipe, where the high viscosity pump is configured to fill with the drilled cuttings while transferring the drilled cuttings from the sampler unit;
     a scale configured to weigh the high viscosity pump and the drilled cuttings filling the high viscosity pump;
     an inflow door fixed to the high viscosity pump and configured to be open while filling the high viscosity pump with the drilled cuttings;
     an outflow door fixed to the high viscosity pump and configured to be closed while filling the high viscosity pump with the drilled cuttings;
   a washer unit configured to remove debris from the drilled cuttings;
   a second flexible pipe configured to transport the drilled cuttings from the sampler unit to the washer unit;
   an analysis unit configured to determine lithological properties of the drilled cuttings;
   a packager unit configured to package the drilled cuttings; and
   a central processing unit (CPU) configured to coordinate operations to process the drilled cuttings through each of the sampler unit, washer unit, analysis unit and packager unit; and
   wherein the CPU facilitates a processing link among the sampler unit, washer unit, analysis unit and packager unit such that the sampler unit, washer unit, analysis unit and packager unit are integrated to form the modular system,
   wherein the lithological properties of the drilled cuttings comprise a grain pattern, a grain shape, and a porosity of the drilled cuttings,
   wherein the CPU is configured to actuate the inflow door and the outflow door according to a predetermined sampling frequency such that the drilled cuttings are received with the high viscosity pump and weighed by the scale at predetermined drilling intervals.

2. The modular system of claim 1, wherein the washer unit is further configured to rotate around a central axis while fluid is pumped through the washer unit.

3. The modular system of claim 2, wherein the washer unit comprises a plurality of sieves disposed coaxially with the central axis of the washer unit.

4. The modular system of claim 3, wherein the analysis unit comprises a plurality of sensors, and each sensor of the plurality of sensors of the analysis unit is disposed on a separate retractable stand, such that a height of each sensor is adjusted to a required distance between each sensor and the drilled cuttings.

5. The modular system of claim 1, wherein the analysis unit comprises a plurality of sensors including a white light camera, an ultraviolet camera, and an x-ray frequency spectrometer.

6. The modular system of claim 1, wherein the packager unit comprises a robotic arm that is configured to transport the drilled cuttings from a sample tray to a sample package.

7. The modular system of claim 6, wherein the robotic arm is further configured to stack a plurality of sample packages into a sample container.

8. The modular system of claim 1, wherein the CPU is further configured to transmit the lithological properties of the drilled cuttings to a database.

9. The modular system of claim 1, wherein the system is configured to be transiently installed at a wellsite.

10. A method for analyzing drilled cuttings, the method comprising:
    receiving drilled cuttings with a first flexible pipe of a sampler unit from a shale shaker disposed on a rig site and configured to obtain the drilled cuttings;
    filling a high viscosity pump of the sampler unit with the drilled cuttings while transferring the drilled cuttings from the sampler unit, where the high viscosity pump is fluidly connected to the first flexible pipe;
    actuating an inflow door of the sampler unit that is fixed to the high viscosity pump such that the inflow door is open while the high viscosity pump is filling with the drilled cuttings;
    actuating an outflow door of the sampler unit that is fixed to the high viscosity pump such that the outflow door is closed while the high viscosity pump is filling with the drilled cuttings;
    weighing the high viscosity pump and the drilled cuttings filling the high viscosity pump with a scale of the sampler unit;
    transporting the drilled cuttings from the sampler unit to a washer unit with a second flexible pipe;
    removing debris from the drilled cuttings with the washer unit;
    determining lithological properties of the drilled cuttings;
    packaging the drilled cuttings;
    coordinating operations for processing the drilled cuttings with a Central Processing Unit (CPU) in order to perform the above steps of receiving the drilled cuttings, removing debris, determining lithological properties, and packaging the drilled cuttings; and
    facilitating a processing link with the CPU to perform the coordinated operations such that the coordinated operations are performed by a modular system,
    wherein the lithological properties of the drilled cuttings comprise a grain pattern, a grain shape, and a porosity of the drilled cuttings, and
    wherein the inflow door and the outflow door are actuated by the CPU according to a predetermined sampling frequency such that the drilled cuttings are received with the high viscosity pump and weighed by the scale at predetermined drilling intervals.

11. The method of claim 10, wherein removing the debris from the drilled cuttings comprises rotating the drilled cuttings around a central axis while fluid is pumped over the drilled cuttings.

12. The method of claim 11, wherein removing the debris from the drilled cuttings further comprises filtering the debris from the drilled cuttings with a plurality of sieves disposed coaxial to the central axis.

13. The method of claim 10, wherein determining the lithological properties of the drilled cuttings comprises analyzing infrared, ultraviolet, and x-ray frequencies of the drilled cuttings.

14. The method of claim 10, wherein determining the lithological properties of the drilled cuttings further comprises adjusting a height of a plurality of sensors such that the height of each sensor of the plurality of sensors is adjusted to a required distance between each sensor and the drilled cuttings.

15. The method of claim 10, wherein packaging the drilled cuttings further comprises transporting the drilled cuttings from a sample tray to a sample package and labelling the sample package.

16. The method of claim 15, wherein packaging the drilled cuttings further comprises stacking a plurality of sample packages into a sample container.

17. The method of claim 10, further comprising controlling the reception of the drilled cuttings, the removal of the debris from the drilled cuttings, the determination of the lithological properties of the drilled cuttings, and a transmission of the lithological properties of the drilled cuttings with the central processing unit.

* * * * *